(12) United States Patent
Johnson

(10) Patent No.: US 11,951,087 B2
(45) Date of Patent: Apr. 9, 2024

(54) EYE WASH COMPOSITIONS AND METHODS

(71) Applicant: Lanny Leo Johnson, Frankfort, MI (US)

(72) Inventor: Lanny Leo Johnson, Frankfort, MI (US)

( * ) Notice: Subject to any disclaimer, the term of this patent is extended or adjusted under 35 U.S.C. 154(b) by 0 days.

(21) Appl. No.: 17/813,760

(22) Filed: Jul. 20, 2022

(65) Prior Publication Data

US 2023/0030714 A1    Feb. 2, 2023

Related U.S. Application Data

(60) Provisional application No. 63/203,618, filed on Jul. 27, 2021.

(51) Int. Cl.

| | | |
|---|---|---|
| *A61K 31/192* | (2006.01) | |
| *A61K 31/14* | (2006.01) | |
| *A61K 31/205* | (2006.01) | |
| *A61K 31/496* | (2006.01) | |
| *A61K 47/10* | (2017.01) | |
| *A61K 47/26* | (2006.01) | |
| *A61K 47/60* | (2017.01) | |
| *A61L 12/12* | (2006.01) | |
| *A61L 12/14* | (2006.01) | |

(52) U.S. Cl.
CPC ............ *A61K 31/192* (2013.01); *A61K 31/14* (2013.01); *A61K 31/205* (2013.01); *A61K 31/496* (2013.01); *A61K 47/10* (2013.01); *A61K 47/26* (2013.01); *A61K 47/60* (2017.08); *A61L 12/12* (2013.01); *A61L 12/141* (2013.01); *A61L 12/143* (2013.01)

(58) Field of Classification Search
CPC .... A61K 31/14; A61K 31/192; A61K 31/205; A61K 31/496; A61K 47/10; A61K 47/26; A61K 47/60; A61K 49/0008; A61L 12/12; A61L 12/141; A61L 12/143; A61L 12/08; A61L 12/14
See application file for complete search history.

(56) References Cited

U.S. PATENT DOCUMENTS

| | | | |
|---|---|---|---|
| 7,923,469 B2 | 4/2011 | Huth et al. | |
| 10,507,191 B2 | 12/2019 | Twomey et al. | |
| 2008/0119550 A1* | 5/2008 | Qin | A61K 9/0007 |
| | | | 514/568 |
| 2015/0133409 A1* | 5/2015 | Parikh | A61K 31/496 |
| | | | 514/171 |
| 2017/0319515 A1* | 11/2017 | Shabto | A61P 31/04 |

FOREIGN PATENT DOCUMENTS

WO    WO-2021001366 A1 *    1/2021    ........... A61K 31/573

OTHER PUBLICATIONS

Okahara et al., The J. Toxicological Sciences, 2013, vol. 38(4), pp. 531-537 (Year: 2013).*
Allen, U.S. Pharmacist, 2015, vol. 40(6), pp. 1-6 (Year: 2015).*
European Commission, Health & Consumer Protection Directorate-General, "Scientific Committee on Consumer Products SCCP, Opinion on Benzoic Acid and Sodium Benzoate", Adopted by the SCCP during the 4th plenary of Jun. 21, 2005, SCCP/0891/05.
Wikipedia, the free encyclopedia, "Chlorhexidine", last edited: Jun. 12, 2021.
Wikipedia, the free encyclopedia, "Contact lens", last edited: Jul. 19, 2021.
Wikipedia, the free encyclopedia, "Ophthalmic drug administration", last edited: Jun. 14, 2021.
Wikipedia, the free encyclopedia, "Pathogenic bacteria", last edited: Jun. 25, 2021.
Wikipedia, the free encyclopedia, "Protocatechuic acid", last edited: Jun. 7, 2021.
Wikipedia, the free encyclopedia, "Saline (medicine)", last edited: Jul. 3, 2021.
Wikipedia, the free encyclopedia, "Sterilization (microbiology)", last edited: Jul. 12, 2021.
Wikipedia, the free encyclopedia, "Benzalkonium chloride", last edited: Jun. 14, 2022.

* cited by examiner

*Primary Examiner* — Sarah Pihonak
(74) *Attorney, Agent, or Firm* — Stonebridge IP, PLLC

(57) ABSTRACT

This disclosure provides a method of treating an infection or inflammation of an eye of a mammal including contacting an eye with a solution comprising sterilized water and protocatechuic acid. The protocatechuic acid may be between about 0.01 wt % and 1.25 wt % in the solution. The solution may include saline. The solution may include ciprofloxacin and/or norfloxacin. This disclosure further provides a method of disinfecting a contact lens including contacting a contact lens with a solution including protocatechuic acid. The solution may include a surfactant. The surfactant may include polyethylene glycol esters of fatty acids, coconut, polysorbate, polyoxyethylene or polyoxypropylene ethers of high alkanes C12-C18. The surfactant may include poly (oxypropylene)-poly(oxyethylene) adducts of ethylene diamine having a molecular weight about 7,500 to about 27,000 wherein at least about 40 weight percent of the adducts is poly(oxyethylene).

7 Claims, No Drawings

EYE WASH COMPOSITIONS AND METHODS

CROSS REFERENCE TO RELATED APPLICATIONS

This application claims priority to U.S. 63/203,618 filed on Jul. 27, 2021 which is herein incorporated by reference in its entirety.

BACKGROUND OF THE DISCLOSURE

Field of the Invention

The present disclosure is directed to solutions for the treatment of infections of an eye of a mammal and solutions for disinfecting contact lens.

Description of the Related Art

Many health conditions are characterized by infection and/or inflammation, such as various conditions of the eyes. Such conditions may be treated with, for example, topical or systemic antibiotics, antivirals, and/or anti-inflammatory agents depending on the suspected etiology. Such treatments are however limited by microbial resistance, drug toxicity, irritation, and/or hypersensitivity that may develop. Methods and compositions for broadly, effectively, and safely treating infected regions and/or inflammatory conditions of the eye are needed.

For example, conjunctivitis, commonly known as pink eye, is an inflammation of the conjunctiva, the outer-most layer of the eye that covers the sclera. While many of the signs and symptoms of conjunctivitis are relatively non-specific, there are several etiologies that may be causative in a given case. The three most common causes of conjunctivitis are bacterial infection, viral infection, or an allergic reaction.

Bacterial conjunctivitis is commonly caused by *Staphylococcus* and *Streptococcus* bacteria, and in the case of newborns, may result from vertical transmission of *Neisseria* or *Chlamydia* from an infected mother. The symptoms and the severity of bacterial conjunctivitis depend on the bacteria involved. For example, when caused by a pyogenic bacterium, the infection may produce a stringy, opaque discharge that may cause matting of the eyelids. There may be severe crusting of the infected eye and surrounding skin. Where bacterial conjunctivitis is suspected, the condition is treated with an antibiotic effective for a broad range of bacteria. Where initial antibiotic treatment is unsuccessful, bacterial cultures can be initiated to guide treatment, although negative results are common since some bacteria implicated in conjunctivitis are not easily cultured by usual laboratory culturing methods. Bacterial conjunctivitis can be contagious, and easily spreads from one eye to the other and from person to person. Ear infections also commonly occur in children with persistent bacterial conjunctivitis.

Viral conjunctivitis may be associated with an upper respiratory tract infection, cold, or sore throat and may be caused by adenovirus. Viral conjunctivitis sometimes produces a water discharge. While the infection runs its course, the symptoms of viral conjunctivitis can be relieved with cool compresses and artificial tears. For more severe cases, topical steroid drops may be prescribed to reduce the discomfort from inflammation. These are not without side effects, especially with prolonged use.

Allergic conjunctivitis occurs more frequently among those with allergic conditions and may be caused by intolerance to substances such as cosmetics, medications, or fumes. For allergic conjunctivitis, cool compresses and artificial tears sometimes relieve discomfort in mild cases. In more severe cases, non-steroidal anti-inflammatory medications and antihistamines may be prescribed. Some patients with persistent allergic eye infections may also require topical steroid drops.

Blepharitis is an inflammation of the eyelid margins and is usually caused by an infection of *Staphylococcus aureus*. Treatment generally involves cleaning the lid and applying a topical antistaphylococcal antibiotic. Blepharitis can lead to a chalazion or lead to a stye (hordeolum). A chalzion is a cyst in the eyelid caused by inflammation of a blocked meibomian gland, usually on the upper eyelid. A chalazion may spawn bacterial infection. When the condition does not resolve on its own, a chalazion may be injected with corticosteroid or be surgically removed.

Hordeola include both external hordeolum, or stye, and internal hordeolum (acute meibomianitis). Styes are lesions at the base of the eyelashes and are predominantly caused by infection of *Staphylococcus aureus*. Treatment may involve draining and topical application of an antibiotic to the lesion.

Infections may afflict the lacrimal system of the eye, such as canaliculitis and dacrocystitis. Canaliculitis can be caused by *Actinomyces* infection and treatment typically involves mechanical expression of the exudative or granular material from the canaliculi, combined with probing and irrigation of the nasolacrimal system with a penicillin eyedrop solution. Dacrocystitis is often due to streptococci or *Staphylococcus aureus* and is usually treated with antibiotics.

Compositions that provide a broadly effective and safe treatment for conditions characterized by infection e.g., bacterial, viral, and/or fungal, and/or inflammation including acute and chronic inflammation, as well as delayed-type and immediate-type hypersensitivity, so as to avoid development of bacterial resistance to antibiotics, and so as to avoid toxicity, irritation, and/or hypersensitivity that may occur with conventional agents are needed.

One concern with current contact lens care, in-the-eye rewetting, artificial tear solutions and eye wash solutions, and the surfactants therein, pertains to a lack of beneficial effects on ocular tissues. Existing surfactants clean well, but do not provide additional benefits to the ocular tissues. Another concern with current surfactants pertains to systemic absorption. A significant amount of any solution, which is placed into the eye, is washed out, for example, through the nasolacrimal ducts into the gastrointestinal tract. Current surfactants, despite being compatible with lens care solutions and comfortable to the eye, are not known to be metabolically degraded or useful.

It would therefore be advantageous to provide contact lens care compositions and compositions for use in the eye, and methods for using such compositions, including surfactants which provide one or more additional benefits, for example, to ocular tissues and/or systemically to the human or animal in whose eye the composition is placed.

SUMMARY OF THE INVENTION

This disclosure provides a method of treating an infection or inflammation of an eye of a mammal including contacting an eye with a solution comprising sterilized water and protocatechuic acid. The protocatechuic acid may be between about 0.01 wt % and 1.25 wt % in the solution. The solution may include saline. The solution may include ciprofloxacin and/or norfloxacin.

This disclosure further provides a method of disinfecting a contact lens including contacting a contact lens with a solution including protocatechuic acid. The solution may include a surfactant. The surfactant may include polyethylene glycol esters of fatty acids, coconut, polysorbate, polyoxyethylene or polyoxypropylene ethers of high alkanes C12-C18. The surfactant may also include includes poly(oxypropylene)-poly(oxyethylene) adducts of ethylene diamine having a molecular weight about 7,500 to about 27,000 wherein at least about 40 weight percent of the adducts is poly(oxyethylene). The surfactant may include a polyoxyethylene and/or polyoxypropylene block copolymer.

Other features and aspects will be apparent from the following detailed description, the drawings, and the claims.

DETAILED DESCRIPTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

In one aspect, the present invention provides a method for treating an ocular condition involving infection and/or inflammation, including acute and chronic inflammation, as well as delayed-type and immediate-type hypersensitivity. Such conditions include those affecting the conjunctiva, uvea, eye lids, oil glands, and lacrimal ducts, such as: bacterial, viral, or allergic conjunctivitis, uveitis, blepharitis, external and internal hordeolum, canaliculitis, dacrocystitis, and chalazions. The lacremal duct removes fluid to the nasopharynx and therefore provides a route to the pulmonary tree with infective pathogens.

This disclosure describes administering a solution including protocatechuic acid (PCA) to the affected area. This disclosure provides a broadly effective method for cleansing and treating the inflamed and/or infected regions, and in a manner relatively independent of the etiology of the inflammation or infection, and in a manner that is free of toxicity and hypersensitivity. The methods are useful as an alternative, or adjunct therapy, to conventional antibiotics, antivirals, decongestants, antihistamines, and steroid treatments, or as an alternative to therapy using a combination of conventional medicaments.

In a second aspect, this disclosure provides a composition containing protocatechuic acid (PCA) for treating inflamed and/or infected regions of the eye and a pharmaceutically acceptable carrier or in a solution.

In another aspect, this disclosure relates to solutions and methods for contact lens care and eye care. More particularly, this disclosure describes compositions which include protocatechuic acid (PCA) and methods of contact lens care using the solutions. Contact lenses are thin lenses placed directly on the surface of the eyes and can be worn to correct vision or for cosmetic or therapeutic reasons. See Contact lens, Wikipedia, the free encyclopedia, last edited 19 Jul. 2021, herein incorporated by reference.

A solution of the disclosure may include PCA and have a pH of from about 4 to about 7. A composition of the disclosure is broadly effective for cleansing, disinfecting, and/or reducing inflammation of the eyes. The solutions of the disclosure are useful as an alternative or adjunct to conventional treatments, and are particularly suitable for prolonged use and hygiene, especially for individuals prone to such infections and/or inflammatory conditions, or individuals that typically experience hypersensitivity with other treatments.

The present disclosure relates to compositions and methods for contact lens care and eye care. More particularly, the invention relates to compositions and solutions which include protocatechuic acid and to methods of contact lens care and eye care using such compositions.

Protocatechuic acid is advantageous for use in contact lens care and eye care applications due to is anti-oxidation, anti-inflammation, anti-bacterial, and anti-viral properties. Protocatechuic acid may be used alone in liquid solution and or with other lens care liquid multipurpose solutions.

Protocatechuic acid is soluble in a lens care solution, non-irritating to eye tissues and has a hydrophilic-lipophile balance (HLB) of about 12.4 to about 18.8. Satisfactory non-ionic surfactants include, without limitation, polyethylene glycol esters of fatty acids, e.g., coconut, polysorbate, polyoxyethylene or polyoxypropylene ethers of high alkanes (C12-C18).

One group of non-ionic surfactants, poly(oxypropylene)-poly(oxyethylene) adducts of ethylene diamine having a molecular weight about 7,500 to about 27,000 wherein at least about 40 weight percent of the adducts is poly(oxyethylene), are advantageous for use in cleaning and conditioning both soft and hard contact lenses when used in amounts from about 0.01 to about 15 weight percent. The CTFA Cosmetic Ingredient Dictionary's adopted name for this group of surfactants is poloxamines. An analogous series of surfactants is the poloxamer series, which are polyoxyethylene, and polyoxypropylene block polymers.

PCA is present in the human diet and is readily absorbed and metabolized. Upon ingestion PCA perfuses the entire body. It has peak amount in 2 hours and lasts 8 hours. It is eliminated via the urine and feces. PCA is 10 times more powerful of an antioxidant than vitamin E. See e.g., Protocatechuic acid, Wikipedia, the free encyclopedia, last edited: 7 Jun. 2021, herein incorporated by reference.

In embodiments the disclosure also provides a system for minimally invasive surgery (MIS) wherein the system comprises a tube that is adapted for receiving a PCA solution from a reservoir and the tube is further configured to deliver the PCA solution to a site in a patient where surgery is being performed including the eye, wherein the system further includes a reservoir containing a solution of up to 1.24% PCA in sterilized water.

Advantageously, the antimicrobial solutions are useful against drug resistant microbes, including MRSA and *Pseudomonas aeruginosa*.

The solutions may further include chlorhexidine. See Chlorhexidine, Wikipedia, the free encyclopedia, last edited 12 Jun. 2021, herein incorporated by reference.

Saline as used herein generally refers to a mixture of sodium chloride in water used for medical purposes. See Saline (Medicine), Wikipedia, the free encyclopedia, date of last revision 3 Jul. 2021, herein incorporated by reference.

Sterilization refers to a process that removes, kills, or deactivates microorganisms such as fungi, bacteria, spores, unicellular eukaryotic organisms such as *Plasmodium*, etc. See Sterilization (microbiology), Wikipedia, the free encyclopedia, last edited: 12 Jul. 2021, herein incorporated by reference.

Contacting an eye with a solution as referred to herein can generally refer to known and established methods of ophthalmic drug and solution administration including eye drops, solution flow, sprays, gels, ointments, etc. See e.g., Ophthalmic drug administration, Wikipedia, the free encyclopedia, last edited 14 Jun. 2021, herein incorporated by reference.

The solutions may further include a stabilizer or preservative examples of which include benzalkonium chloride (BAK; detergent), chlorobutanol (Cbl; detergent), methyl paraben (MP; chelating agent), sodium perborate (SP; oxidative agent), and stabilized thimerosal (Thi; organomercurial); BAK is preferred and is typically used in concentrations varying from 0.015% to 0.05% by weight for contact lens solutions and 0.005% to 0.01% by weight for eye wash solutions. See e.g., benzalkonium chloride, Wikipedia, the free encyclopedia, last edited: 14 Jun. 2022, herein incorporated by reference. Disodium-ethylene diamine tetra-acetate (EDTA) and/or phosphate-buffered saline may also be added as buffering agents. The solutions can contain benzoic acid and sodium benzoate.

Bacterial as referred to herein generally refers to pathogenic bacteria, particularly those that can affect the eye. See Pathogenic bacteria, Wikipedia, the free encyclopedia, last edited 25 Jun. 2021, herein incorporated by reference.

The disclosed formulations may find use as Moisturizers/Lubricants, Allergy & Redness Relief, Antibiotic/Antimicrobial solutions, and/or for Eyewash compositions for both human & veterinary use. The disclosed formulation may also be used for contact lens care including cleaning and disinfecting contact lenses and also as an antimicrobial coating on a lens.

Example 1

Use of In Vitro Studies for Antimicrobial Susceptibility Testing of Anthocyanins, Anthocyanidins, or Metabolites and Compounds Thereof.

This example describes the method for testing the antimicrobial susceptibility of anthocyanins, anthocyanidins, or metabolites and compounds thereof. The Kirby-Bauer method of disc diffusion was used for testing, following a standard set of procedures recommended by the NCCLS. In this methodology, a set of discs saturated with either testing compounds or a control was placed on inoculated agar plates. The plates were inoculated with organisms including *C. difficile, P. acnes, C. prefringens, L. casei, C. albicans, E. coli*, ATTC 8739 and ATCC 43895, *S. aureus, S. mutans, S. pyogenes, P. aeruginosa* and *K. pneumonia*. The control sample was amoxicillin, an antimicrobial with very effective broad-spectrum antibiotic properties. Samples included delphinidin, pelargonidin, cyanidin CI, 28% cyanindin-3-glucoside (C3G), protocatechuic acid (PCA) and 2,4,6 Trihydroxybenzaldehyde (2,4,6 THBA).

After 18, 24, or 48 hours of incubation, depending upon the microorganism, each plate was examined. The diameters of the zones of complete inhibition were measured, including the diameter of the disc. Zones were measured to the nearest millimeter, using sliding calipers. The size of the zones of inhibition was interpreted by referring to NCCLS standard. Results were interpreted as follows: NI was no inhibition of growth under the test sample, I was inhibition of growth under the test sample, NZ indicated no zone of inhibition surrounding the test sample, and CZ indicated a clear zone of inhibition surrounding the sample and zone width in millimeters.

Results

The testing samples had bactericidal and bacteriostatic activity against many of the organisms. Of note, *P. acnes*, an organism that is very difficult to treat, often requiring multiple current antibiotics for effective treatment, was susceptible to both C3G and PCA. Indeed, both of these test samples were bactericidal against *P. acnes*. Additionally, PCA was also effective against *Staphylococcus aureus* ATCC 33591, known as Methacillin Resistant Staph *Aureus* (MRSA).

PCA was also shown to have some effectiveness against *Pseudomonas aeruginosa*, a common pathogen in wounds, especially burns. Amoxicillin, the control sample, had no effect on *P. aeruginosa*. Similarly, *Candida albicans*, frequently a co pathogen in wounds, was susceptible to PCA.

In summary, the present invention provides advantages over the prior art, including providing anthocyanin, anthocyanidin, their metabolites or combinations thereof to a wound to provide a reduction or elimination of bacteria. It is contemplated that the invention will also find use in the treatment of surfaces, including medical devices and medical implants, to reduce or eliminate bacteria.

Example 2

Use of Mouse Model to Determine Dose Levels and Intervals of Test Samples

Methods:

Mice had back skin tape stripped and the stripped site (wound) was infected with *P. aeruginosa* (ACTA 9027). The test reagents were applied topically in an aqueous solution on the stripped site at two hours and daily for four days.

Cyanidin 3-glucoside (C3G), an anthocyanin, and its main metabolite PCA were formulated and tested at several doses. The aqueous carrier was water. The C3G formulation included 50 mM, 100 mM and 200 mM dose concentrations. Similarly, the PCA formulation included at 50, 100 and 200 mM dose concentrations.

Results

Results were collected from the mice at day five. Both C3G and PCA decreased the bacterial burden; however, none were statistically significant. There was a trend towards a decreasing concentration of PCA, with 50 mM being the most effective. The most effective dose of C3G was 100 mM. It is contemplated that because C3G degrades to PCA in this environment, the test results may indicate that C3G was not being tested alone, but rather was a combination of C3G and its metabolites, including a combination of C3G and PCA as the effective agents.

Example 3

Use of Mouse Model to Further Determine Effective Dose Levels and Dose Intervals of Test Samples Methods:

Mice had back skin tape stripped and the stripped site (wound) was infected with *P. aeruginosa* (ACTA 27853). The test reagents were applied topically in an aqueous solution on the stripped site at two hours and daily on day 1, 2 and 3.

C3G, an anthocyanin and its main metabolite PCA were formulated and tested at several doses. The aqueous carrier was water. The C3G formulation included 100 mM and 200 mM dose concentrations and the PCA formulation included 25 and 50 mM dose concentrations.

Results

Results were collected from the mice at day two and four. Both C3G and PCA decreased the bacterial burden at 48 and 96 hours. The most significant decrease of bacteria was observed at 25 mM of and 100 and 200 mM of C3G. Although PCA at 25 mM reduced the bacterial burden at both time periods, its activity was statistically significant at 48 hours. C3G at both 100 mM and 200 mM significantly reduced the bacterial burden at 48 and 96 hours.

Example 4

Use of a Mouse Model for Wound Healing
Methods:
Mice were shaved but unstrapped and uninfected (normal rodent skin). The test reagents were applied topically in an aqueous solution on the unstripped site at two hours and daily on day 1, 2 and 3.
Testing reagents consisted of C3G and PCA formulated at one dose, 100 µM in an aqueous solution.
Results
There was little or no stimulation of IGF-1 and TGF-β at local levels observed at the 100 µM concentration of testing reagents. In fact, levels of EGF actually decreased below normal levels. There was observed a decrease of all three local growth hormones at 100 µM of C3G. These results suggest that mice skin differs in response to a dose that has been shown to stimulate human synovium to produce IGF-1. Thus, this low of a dose is not useful for rodents for this purpose.

Example 5

Use of Mouse Model to Determine Isolated Effect of 25 mM Solution of PCA in Various Environments
Methods:
Four different conditions were used: mice had back skin tape stripped and the stripped site (wound) was infected with *P. aeruginosa*; mice had back skin stripped and were not infected, mice had taped stripped, infected and treated with PCA, mice were tape stripped, uninfected, and treated with PCA. When used, the PCA test reagent was applied topically in an aqueous solution on the stripped site at two hours and 24 hours.
The testing reagents consisted of and PCA formulated at one dose, 25 mM, in an aqueous solution. Levels of IGF-1, TGF-β, and EGF levels in the skin tissue at 48 hours were measured by ELISA. There were two control groups: the stripped skin and the stripped skin and infected.
Results
The infected stripped skin showed the highest level with IGF-1 (statistically significant) and TGF-β. This is representative of tissue response to injury and infection; similarly, the EGF response was very inconsistent compared to the other two growth hormones.
The EGF response levels were different than either IGF-1 or TGF-β. They were highest in the stripped and uninfected wound and lowest in the stripped, infected and treated wound. Therefore, the treatment optimized the amount of hormone production compared to the untreated infection. This is beneficial to limit scarring while promoting healing over the controls. Overall, PCA at 25 mM acts on stripped and infected mice skin and optimizes the IGF-1 production and optimizes the local growth hormones.

Example 6

Use of Mice to Establish Wound Promoting Effect of Compositions
Method:
Fifteen rodents were used to establish the histological findings of stripped skin, stripped and infected skin, and stripped, infected and treated wound. There were two control groups and four experimental groups according to the following:
Control Group 1: three mice with only tape stripped wounds on the back. These mice were not infected or treated. The skin was harvested at time zero, 2 and 48 hours for histology examination.
Control Group 2: three had tape stripped wounds and infection. Tissue submitted at 2 and 48 hours for histological examination.
Experimental Groups: There were 4 experimental groups. In these groups, mice had skin stripped wounds and infection. Treatment varied by reagent and dosage. Testing reagents included PCA at 25 at 25 and 50 mM and C3G at 100 and 200 mM.
*Pseudomonas aeruginosa* (ATCC 27853) procured from American Type Culture Collection, Manassas, Va. was used to infect the experimental groups of mice. The organism was grown overnight at 37° C. at ambient atmosphere trypticase soy agar plates supplemented with 5% sheep blood cells. The culture will be aseptically swabbed and transferred to tubes of trypticase soy broth. The optical density will be determined at 600 nm. The cultures will be diluted to provide an inoculum of approximately 9.0 log 10 CFU per mouse in a volume of 100 µL. Inoculum count was estimated before inoculation by optical density and confirmed after inoculation by dilution and back count.
The testing reagents were topically applied at 2 and 24 hours with 100 µL of fluid spread over the wound.
The following histological assessments were conducted:
Surface Cellularity: The histological assessment included the presence or absence of the surface cellularity and the depth of the cells.
Dermis:
Thickness: The thickness of the dermal layer was observed.
Hair Follicles: The hair follicles and the layer of surrounding cells were observed. Hair follicles presence is critically important to skin wound healing. (Gharzi A, Reynolds A J, Jahoda C A. Plasticity of hair follicle dermal cells in wound healing and induction. Exp Dermatol. 2003 April; 12 (2):126-36). The dermal sheath surrounding the hair follicle has the progenitor cells for contributing fibroblasts for wound healing. (Johada C A, Reynolds A J. Hair follicle dermal sheath cells: unsung participants in wound healing. Lancet. 2001 Oct. 27; 358(9291):1445-8).
Vascularity: Vascularity was observed, but an assessment of angiogenesis was not performed on the 48-hour material since new vascularity takes three to twelve days to develop. (Busuioc C J, et al. Phases of cutaneous angiogenesis process in experimental third-degree skin burns: histological and immunohistochemical study. Rom J Morphol. Embryol. 2013; 54(1):163-710.)
Inflammation: The presence of cellular infiltration was observed and its location.
Skin Thickness: The thickness of the skin was estimated related to the uninfected, untreated wound. This depth was estimated on the uniform histology photomicrographs from the surface to the muscle layer.
Results
The following results were observed in each group:
CONTROL GROUP 1: Uninfected and untreated.
Time Zero: At time zero following the wound stripping there was cellular covering of the surface. The dermal layer was not thickened. The hair follicles have a single cellular lining. There was minimal vascularity and no inflammation. The depth of the tissue was considered zero for future benchmark. 0+

2 hours: At 2 hours following the wound stripping the surface remained covered with cellularity. The dermal layer was minimally thickened. The follicles and cellular lining were the same. There was minimal increase in vascularity and inflammation. The increase in the depth of the tissue was considered 0.5+.

48 hours: At 48 hours the wound stripped, uninfected, untreated specimens showed natural history response of surface cellular proliferation and thickness. The dermal layer was thickened. The hair follicles were present with single layer cellular lining. The vascularity was increased in amount compared to the 2-hour specimens. The inflammation was present throughout the dermis and muscle layer. The thickness was considered 0.5+.

CONTROL GROUP 2: Infected and untreated.

2 hours: The histological assessment showed the wound stripped, infected, but untreated controls at 2 hours to have multiple cellular covering on surface. There was minimal thickening of the dermal layer. The hair follicles were abundant and had double layer cellular lining. There was minimal vascularity and no inflammation in the specimens. The thickness was assigned 0.5+.

48 hours: At 48 hours the surface cellular covering was gone. The dermal layer had minimal thickening. The hair follicles were present, with minimal cellularity lining. There was marked increase in vascularity and minimal inflammation in dermis layer. The depth was considered 0.5+ compared to time zero.

Experimental Group PCA 25 Mm 48 hours: The cellular covering of the surface was abundant and multiple cell layers. The dermal layer was thickened. The hair follicles were prominent with multiple cellular lining. There was collagen proliferation between the epidermis and dermis. Additionally, there was moderate vascularity, but less than that seen in infected untreated group. There was abundant inflammation and it was greater than was seen in the PCA 50 dose. Thickness was assigned 2+.

Experimental Group PCA 50 Mm 48 hours: The surface was covered with multiple layers of cells. The dermal layer was thicker. The hair follicles had double layer of cells. There was increased vascularity. Inflammation also increased in the dermis and below the muscle layer. The tissue thickness was assigned 2+.

Experimental Group C3G 100 Mm

48 Hours: There was multiple cellular covering of the surface. The dye of the C3G was apparent on the skin surface indicating it had not changed color due to pH nor completely degraded. The dermal layer was thicker. The hair follicle had single and double cellular lining. The vascularity was prominent. There was inflammation in the dermis and muscular layer and below. The thickness of the tissue was assigned 2+.

Experimental Group C3G 200 Mm

48 Hours: There was evidence of the C3G material remaining on the skin surface. The surface cellular layer was multiple cells thick. The dermal layer was thickened. The hair follicles had single and double cellular lining. The vascularity was increased. There was inflammation in the dermis and muscular layer. The thickness was assigned 2+.

These results confirm that an anthocyanin ("38% C-3-G as the source) and the main metabolite of anthocyanins and anthocyanidins, protocatechuic acid (PCA) when applied topically at various calculated doses to the stripped skin wound of a rodent were bactericidal in 48 to 96 hours. There was a 10,000-fold kill of *Pseudomonas aeruginosa* in 48 hours with both reagents and dose.

The results also show by histology a simultaneous healing of the experimentally created wound in the same time frame. C-3-G and PCA in two different doses stimulated tissue repair as evidence by histology.

Specifically, the experimental model provided evidence of a histological contrast between the control and experimental groups. At 48 hours, Control Group 2 that was wound stripped and infected showed a clear contrast to the uninfected Control Group 1. In the skin stripped infected group there was loss of the epithelial cellular covering, no follicular cellular proliferation, marked increase in vascularity and little inflammatory response. This histological condition provided clear contrast to the treatment groups. All treatment groups by comparison showed healing response with multiple layer cellular proliferation on the surface, multiple layer cellular proliferation along the hair follicles, less vascularity, but an inflammatory cellular response in the dermis and muscular levels. PCA at a concentration of 25 mM also showed collagen layer formation between the epidermis and dermis. This response is beneficial in the use of anthocyanin and anthocyanidins and metabolites thereof as a cosmetic agent to promote wound healing and improve skin health, including wrinkle reduction or removal. This method of use of anthocyanin and anthocyanidin metabolites, and particularly PCA, is based upon the two-fold response; the collagen layer increase and the skin swelling that increased the depth of the skin.

Example 7

In this example, there are 3 formulations, all using sterile water and different concentrations of PCA. In one formulation ¼% PCA, in a second ½% PCA, and in a third 1.24% PCA. Each formulation has 0.05% benzalkonium chloride. Vial sizes would be 1 ounce and 3 ounces with a fine spray and/or proper. These formulations can be used for the treatment of inflammation and/or infection of the eye.

Example 8

This example can be used for cleansing and cleaning eye glass lens as well as other products that the public commonly pick up and handle to try on, view, etc. This is a problem in retail establishments where customers will not pick up a pair of glasses to try on for fear of a prior handler contaminating them. 4- and 8-ounce spray type bottles can be used. The formulations contain 70% denatured ethanol (providing rapid evaporation), ¼% PCA and 0.05% benzalkonium chloride. At this concentration the PCA is not visible to the naked eye and on the lens does not interfere with viewing. At the end of the day, the following wipes may be used to clean and rule out any unrecognized contamination.

Example 9

This example provides wipes for wiping contact lens for cleaning and disinfection. A canister of wipes (160 count) is provided. The wetting solution is 70% ethanol, 1%. protocatechuic acid and 0.05% benzalkonium chloride. The lens can be wiped as necessary allowed to dry before insertion. Optionally can rinse with sterile water and dry with dry wipe.

While this disclosure includes specific examples, it will be apparent after an understanding of the disclosure of this application has been attained that various changes in form and details may be made in these examples without departing from the spirit and scope of the claims and their equivalents.

The invention claimed is:

1. A method of treating bacterial conjunctivitis, viral conjunctivitis, allergic conjunctivitis, uveitis, blepharitis, external hordeolum, internal hordeolum, canaliculitis, dacrocystitis, or chalazions, in a mammal consisting of:
   contacting an eye of the mammal with a solution consisting essentially of sterilized water and protocatechuic acid.

2. The method of claim 1, wherein the protocatechuic acid is between about 0.01 wt % and about 1.25 wt % in the solution.

3. The method of claim 1, wherein the solution includes saline.

4. The method of claim 1, wherein the solution includes chlorhexidine.

5. The method of claim 1, wherein the solution includes benzalkonium chloride.

6. The method of claim 5, wherein the benzalkonium chloride is present at approximately 0.005 wt % to about 0.01 wt %.

7. A method of treating bacterial conjunctivitis, viral conjunctivitis, allergic conjunctivitis, uveitis, blepharitis, external hordeolum, internal hordeolum, canaliculitis, dacrocystitis, or chalazions, in a mammal consisting of:
   contacting an eye of the mammal with a solution consisting essentially of sterilized water, protocatechuic acid, and one or more selected from the group consisting of: ciprofloxacin, norfloxacin, or a combination thereof.

* * * * *